…

United States Patent [19]
Porz et al.

[11] Patent Number: 5,126,418
[45] Date of Patent: Jun. 30, 1992

[54] ALKENYLAMINOMETHYLENEPHOSPHONIC ACIDS AND COPOLYMERS THEREOF WITH UNSATURATED CARBOXYLIC ACIDS

[75] Inventors: Christoph Porz, Bonn; Gerd Reinhardt; Hermann Hoffmann, both of Kelkheim, all of Fed. Rep. of Germany

[73] Assignee: Hoechst Aktiengesellschaft, Frankfurt am Main, Fed. Rep. of Germany

[21] Appl. No.: 642,519

[22] Filed: Jan. 17, 1991

[30] Foreign Application Priority Data

Jan. 19, 1990 [DE] Fed. Rep. of Germany ....... 4001420

[51] Int. Cl.⁵ .......................................... C08F 230/02
[52] U.S. Cl. .................................. 526/234; 526/266; 526/231; 526/278; 526/240
[58] Field of Search ............... 526/274, 278, 240, 234; 524/807

[56] References Cited

U.S. PATENT DOCUMENTS 4,297,468 10/1981 Chmelir ................................ 526/276
4,678,840 7/1987 Fong ..................................... 525/340

Primary Examiner—Joseph L. Schofer
Assistant Examiner—M. Nagumo
Attorney, Agent, or Firm—Connolly and Hutz

[57] ABSTRACT

Alkenylaminomethylenephosphonic acids of the formula

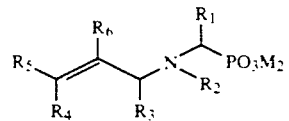

(I)

in which
$R_1$ is hydrogen, $C_4$-$C_{10}$-alkyl, phenyl, naphthyl, methylphenyl, hydroxyphenyl, methoxyphenyl, methylnaphthyl, hydroxynaphthyl or methoxynaphthyl,
$R_2$ is hydrogen,
$R_3$, $R_4$, $R_5$ are hydrogen or methyl,
$R_6$ is hydrogen, $C_1$-$C_4$-alkyl or phenyl, and
M is hydrogen or a cation, and copolymers comprising 0.1-99.9% by weight, preferably 1-50% by weight, of one or more monomers of the formula I, in which $R_2$ is hydrogen or a group of the formula —$CH_2PO_3M_2$, and 99.9-0.1% by weight, preferably 99-50% by weight, of one or more monomers of the formula II $$R_1'R_2'C=CR_3'X \qquad (II)$$

in which
$R_1'$ is hydrogen or a group of the formula —COOM,
$R_2'$ is hydrogen, phenyl or a group of the formula —COOM,
$R_3'$ is hydrogen, methyl or a group of the formula —COOM or —$CH_2$COOM,
X is a group of the formula —COOM or
$R_2'$ and $R_3'$ together are a $C_4$-alkylene or
$R_1'$ X together are a group of the formula

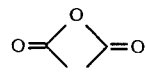

or
$R_3'$ and X together are a group of the formula

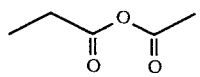

These copolymers are suitable as complexing agents, in particular detergents as builder and co-builder, peroxide stabilizers and as granulating aids for bleaching activators and in crude oil recovery as scale inhibitors having anti-corrosive action.

7 Claims, 1 Drawing Sheet

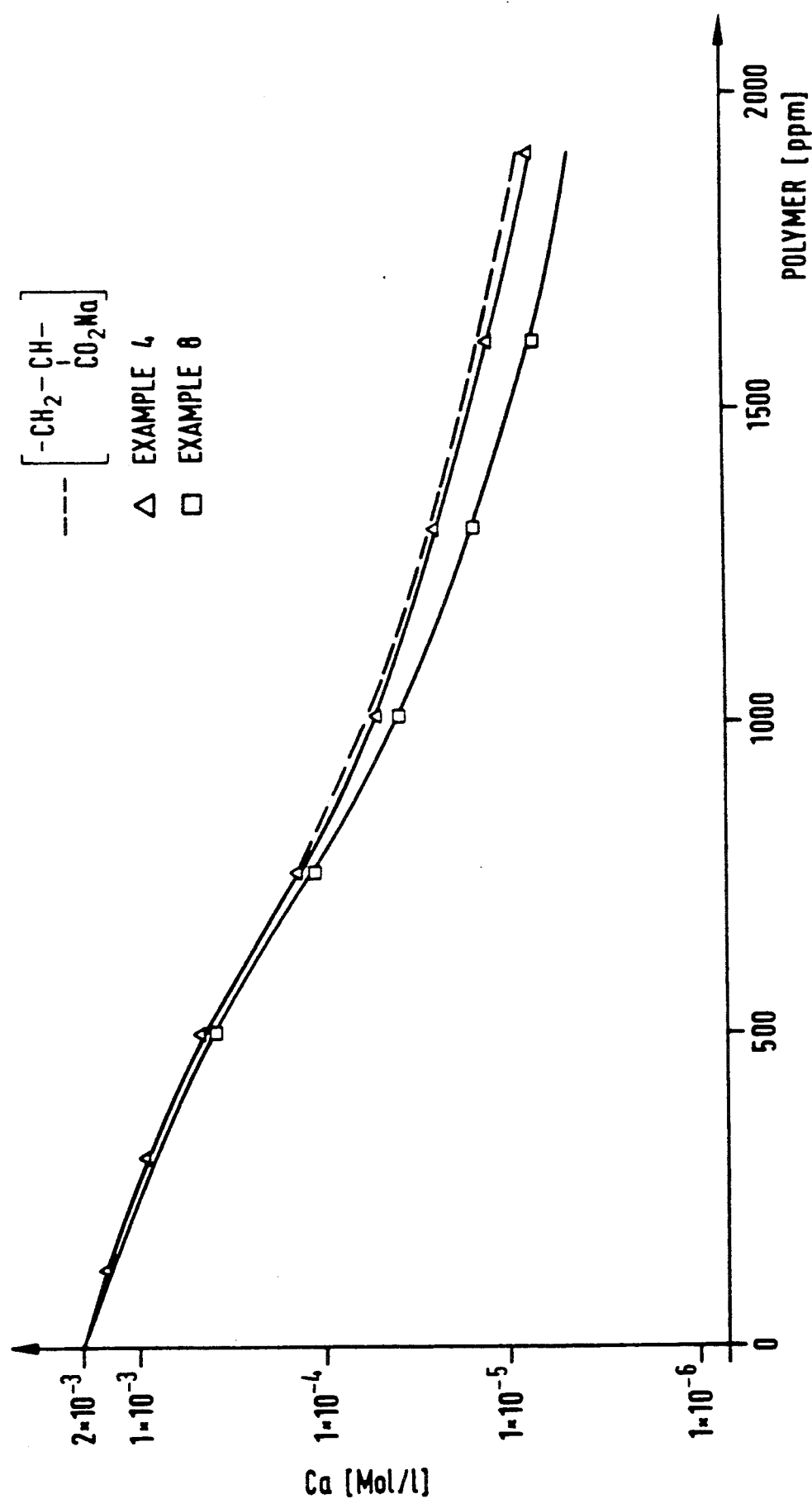

ALKENYLAMINOMETHYLENEPHOSPHONIC ACIDS AND COPOLYMERS THEREOF WITH UNSATURATED CARBOXYLIC ACIDS

BACKGROUND OF THE INVENTION

Low-molecular-weight polyelectrolytes, such as, for example, EDTA, triphosphates, but also aminomethylenephosphonic acids, have wide practical applications, due to their good calcium- and heavy-metal-binding capacity. Thus, aminomethylenephosphonic acids are preferably used in the bleaching wash, since they have a larger heavy-metal-binding constant than EDTA. In detergent formulations, the heavy metals present reduce the shelf life of peroxidized compounds, which leads to a reduced bleaching effect. In textile bleaching, the fibers are damaged by the heavy metal cations.

Apart from these low-molecular-weight polyelectrolytes, high-molecular-weight polycarboxylic acids [M. Ragnetti; Tenside, Surfactants, Detergents 26, 30 (1989); W. Leonhardt, R. Peldszus, H. Wegert; Seifen, Öle, Fette, Wachse 113, 511 (1987)], such as polyacrylic acid, polyhydroxyacrylic acid [K. Henning, J. Kandler, H. D. Nielen; Seifen, Öle, Fette, Wachse 103, 571 (1977) and 104, 7 (1978)], polymaleic acid [German Patent No. 2,405,284] or polyglyoxalic acid [U.S. Pat. No. 4,140,676] in phosphate-free or reduced phosphate detergent formulations have become very important. Compared with the low-molecular-weight polyelectrolytes, the high-molecular-weight polycarboxylic acids as so-called co-builders have clearly improved properties. The co-builder effect on the polycarboxylic acids is probably due to a particularly good transport function of water-soluble metal ions, in particular calcium ions, from the aqueous detergent liquor into the water-insoluble zeolites. Thus, the co-builders function as ion exchanger, since on the one hand they bind calcium and on the other hand have to release calcium into the zeolite. This effect has been described by G. Manning [G. S. Manning in "Polyelectrolytes", Ed. E. Selegny, D. Riedel Publ. Comp. Dordrecht 1974 and G. S. Manning, J. Phys. Chem. 88, 6654 (1984)] by means of his theoretical model of ion condensation.

Furthermore, the high-molecular-weight polycarboxylic acids are used, in addition to low-molecular-weight polyelectrolytes, such as aminomethylenephosphonic acids, in the area of scale inhibition of saline water, i.e. the inhibition to precipitation of sparingly soluble salts of earth metals having anti-corrosive alkaline action. The amounts of polyelectrolyte required for scale inhibition are less than stoichiometric and are in the range from 1-100 ppm. It is assumed that for the so-called "threshold effect" the polyelectrolyte is absorbed on the crystallite surface and thus interferes in or completely prevents the crystal growth. Thus, scale inhibition is of great importance not only in the area of detergent formulations but also in crude oil recovery. Without suitable measures for scale inhibition, saline water deposits would rapidly clog the pores to the well and the producing pipe and prevent an effective crude oil recovery. In practice, polyacrylates are preferably used for inhibition of alkaline metal sulfate depositions, while aminomethylenephosphonic acids are preferably used for inhibition of alkaline earth metal carbonate depositions.

SUMMARY OF THE INVENTION

Surprisingly, it has now been found that unsaturated known and new aminomethylenephosphonic acids can be copolymerized with unsaturated carboxylic acids, and the polymers obtained combine known properties of the different monomers in a single compound. By choosing the monomers, by possibly varying the monomer ratios and by varying the molecular weight of the polymer products, it is thus possible to tailor compounds of the same class of compounds for completely different application objectives.

The invention relates to new alkenylaminomethylenephosphonic acids of the formula I

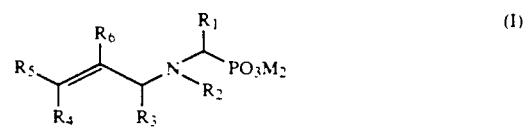

in which $R_1$ is hydrogen, $C_4$-$C_{10}$-alkyl, phenyl, naphthyl, methylphenyl, hydroxyphenyl, methoxyphenyl, methylnaphthyl, hydroxynaphthyl or methoxynaphthyl, preferably phenyl, $R_2$ is hydrogen, $R_3$, $R_4$, $R_6$ are hydrogen or methyl, preferably hydrogen, $R_5$ hydrogen, $C_1$-$C_4$-alkyl or phenyl, preferably hydrogen and M is hydrogen or a cation, preferably sodium, potassium or ammonium.

DETAILED DESCRIPTION

The alkenylaminomethylenephosphonic acids according to the invention are prepared by first reacting a compound of the formula

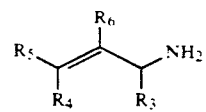

in an organic solvent, for example a lower alcohol having 1 to 5 carbon atoms, chloroform or dimethyl sulfoxide, with an aldehyde of the formula $R_1CHO$ ($R_1$ is as defined above), at temperatures between 0° C. and 100° C., preferably 10° C.-50° C. for 1-10 hours, preferably 2-5 hours, and, if desired, subsequently removing the organic solvent by distillation. The compounds thus obtained of the formula

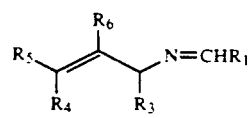

are then further reacted in a solvent or solvent mixture, for example comprising $C_1$-$C_4$-carboxylic acids, such as acetic acid, anhydrides thereof or other polar solvents, with a 1-50%, preferably 1-10%, molar excess of phosphorus acid. The products thus obtained of the formula I are advantageously isolated by precipitation with water or lower alcohols, followed by washing with these solvents.

The invention further relates to new copolymers comprising 0.1-99.9% by weight, preferably 1-50% by weight, of one or more monomers of the formula I, in which $R_2$ is hydrogen or a group of the formula —$CH_2PO_3M_2$, and 99.9-0.1% by weight, preferably 99-50% by weight, of one or more monomers of the formula

in which $R_1'$ is hydrogen or a group of the formula —COOM, $R_2'$ is hydrogen, phenyl or a group of the formula —COOM, $R_3'$ is hydrogen, methyl or a group of the formula —COOM or —CH$_2$COOM, X is a group of the formula —COOM or $R_2'$ and $R_3'$ together are a $C_4$-alkylene radical or $R_1'$ and X together are a group of the formula

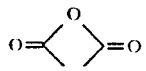

or $R_3'$ and X together are a group of the formula

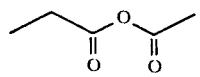

These polymers are composed of 0.1-99.9, preferably 1-50, % by weight of one or more monomers of the formula I and of 99.9-0.1, preferably 99-50, % by weight of one or more monomers of the formula II.

The copolymers according to the invention are prepared by initially introducing compounds of the formula I as pure substances or contaminated with neutralization salts, for example sodium sulfate or sodium chloride, in water or in water-miscible organic solvents, preferably at 20°-100° C., preferably 50°-80° C., and adding compounds of the formula II and a free-radical initiator, for example potassium peroxodisulfate, in succession or simultaneously. If the compounds of the formula I are water-insoluble alkenylaminomethylenephosphonic acids, they are first converted to water-soluble salts, preferably alkali metal salts and ammonium salts. The polymerization is continued at an overall monomer concentration of 5-60% by weight, preferably 10-30% by weight for 1-10 hours, preferably 2-5 hours, at 70°-100° C. The colorless viscous polymer solutions are then brought to the desired pH depending on use, preferably with sodium hydroxide solution, and, if desired, diluted and spray-dried.

The copolymers according to the invention thus obtained can in general be used as complexing agents for alkaline earth metals and heavy metals and in detergents as builders and co-builders, as peroxide stabilizers and granulating aids for bleach activators, for example for tetraacetylethylenediamine and in crude oil recovery as scale inhibitors having anti-corrosive action.

EXAMPLES

The percentages given in all examples are taken to be percent by weight. The inherent viscosity values K were determined according to Ubbelohde.

The $^{31}$P-NMR shifts δ have been measured against phosphoric acid as the standard.

In all examples, deionized water was used. The polymerizations were carried out in 1 l 5-neck flasks with ground glass lid. The flasks are equipped with anchor stirrer, thermometer, reflux condenser, gas inlet tube, addition funnel and heatable water bath. The solutions introduced for polymerization are flushed with nitrogen.

The polymer solutions described in the examples can also be spray-dried or sprayed together with other substances, in particular ingredients of detergents. The acidic polymer solutions (Examples 4, 6 and 8) are, as a rule, brought to a pH between 4 and 5 beforehand. Suitable concentrations for spraying or spray-coating contain about 10% of polymer in the aqueous solution. The anhydrous polymers are white powders which are resolubilizable in water.

EXAMPLE 1

Preparation of N-allylamino(phenyl)methylenephosphonic acid

N-allylbenzylimine is prepared by the literature procedure of M. Bergmann, A. Miekeley, Chem. Ber. 57, 662 (1924). The solvent used is isopropanol instead of diethyl ether, to give the product described in the literature, b.p. 96° C./12 mm Hg, in 95% yield.

In a 500 ml 4-neck flask, equipped with stirrer, contact thermometer, reflux condenser and addition funnel, 82 g (1 mol) of phosphorus acid, 100 g of glacial acetic acid and 20 g of acetic anhydride are initially introduced at 100° C., and 72.5 g (0.5 mol) of N-allyl-benzylimine are added dropwise over a period of about 20 minutes. The mixture is then stirred for 3 hours under reflux. After cooling, the crude solution is stirred in 200 ml of water, which precipitates the product. The filter residue is washed several times and dried at 80° C. and 200 mm Hg of vacuum for 12 hours, giving a 82-87 g (72%-76% of yield) of a colorless crystalline substance having a melting point of 241°-246° C.

$^{31}$P-NMR (D$_2$O/NaOD): δ=16.3 ppm.

EXAMPLE 2

Copolymer prepared from disodium N-allylamino(phenyl)methylenephosphonate and sodium acrylate 36 g of acrylic acid, 0.36 g of N-allylamino(phenyl)-methylenephosphonic acid (Example 1) and 125 g of water are initially introduced, neutralized with 100 g of 20% strength sodium hydroxide solution, and the mixture is heated to 80° C., while introducing a weak stream of nitrogen. At this temperature, the catalyst solution comprising 0.9 g of potassium peroxodisulfate and 20 g of distilled water is added dropwise over a period of 10 minutes. After the exothermic phase, heating at 80° C. is continued for 2 hours, giving a colorless 17% polymer solution having an inherent viscosity value K in the range from 40-45.

EXAMPLE 3

Preparation of a sodium sulfate solution of N-allylaminobis(methylenephosphonic acid)

Allylamine, formaldehyde and phosphorus acid are reacted in a molar ratio of 1:2:2 in a Mannich type reaction, as described by K. Moedritzer and R. R. Irani, J. Org. Chem. 31(5), 1603-7 (1966). In this reaction, sulfuric acid is used instead of hydrochloric acid. This leads to the almost quantitative formation of N-allylaminobis(methylenephosphonic acid).

$^{31}$P-NMR (D$_2$O): δ=8.2 ppm.

Since the water-soluble product can only be isolated in moderate yield, the sulfuric acid is quantitatively neutralized with 33% strength sodium hydroxide solution, and the sodium sulfate product solution thus obtained is used directly for copolymerization (Example 4–6–7).

The solution usually used in the examples comprises 45% by weight of N-allylaminobis(methylenephosphonic acid), 22.5% by weight of sodium sulfate and 32.5% by weight of water.

EXAMPLE 4

Copolymer prepared from N-allylaminobis(methylenephosphonic acid) and acrylic acid N-allylaminobis(methylenephosphonic acid) is used as solution whose composition is as described in Example 3. 22.2 g of this solution are initially introduced together with 182 g of water. The mixture is heated to 80° C. with stirring and while introducing a weak stream of nitrogen. 90 g of acrylic acid and 3 g of potassium peroxodisulfate, dissolved in 53.4 g of distilled water, are added dropwise synchronously from two addition funnels over a period of 3.5 hours. After the addition is complete, the mixture is stirred at 80° C. for another 2 hours, to give a colorless 28.5% strength polymer solution having inherent viscosity values K between 35 and 50 and a sodium sulfate content of 1.4%.

EXAMPLE 5

Terpolymer prepared from disodium N-allylaminophenyl(methylene)phosphonate, sodium acrylate and sodium maleate 6 g of N-allylamino(phenyl)methylenephosphonic acid, 36 g of acrylic acid, 15 g of maleic anhydride and 100 g of water are initially introduced. A neutral salt solution (pH = 7.2) is prepared by adding 150 g of 22% strength sodium hydroxide solution, and the mixture is heated to 80° C. while introducing a weak stream of nitrogen. At this temperature, the catalyst solution comprising 1.8 g of ammonium peroxodisulfate and 40 g of water is added dropwise over a period of 10 minutes. After the exothermic reaction has ceased, the mixture is stirred at 80° C. for another 2 hours, giving a colorless 24.8% strength polymer solution having inherent viscosity values K between 30 and 40.

EXAMPLE 6

Terpolymer prepared from N-allylaminobis(methylenephosphonic acid), acrylic acid and maleic anhydride 13.3 g of N-allylaminobis(methylenephosphonic acid) solution (see Example 3) are initially introduced together with 15 g of maleic anhydride and 92.7 g of water and the mixture is heated to 80° C. with stirring and flushing with nitrogen. At this temperature, 39 g of acrylic acid and 1.8 g of potassium peroxodisulfate, dissolved in 40 g of water, are added dropwise synchronously over a period of 30 minutes. Stirring at 80° C. is then continued for 2 hours. The 29.7% polymer solution contains 1.5% of sodium sulfate, is colorless and has an inherent viscosity value K between 25 and 35. At room temperature, the polymer eventually crystallizes.

EXAMPLE 7

Terpolymer from tetrasodium N-allylaminobis(methylenephosphonate), disodium N-allylamino(phenyl)methylenephosphonate and sodium acrylate 3.6 g of N-allylaminobis(methylenephosphonic acid) solution (see Example 3) are initially introduced together with 1.6 g of N-allylamino(phenyl)methylenephosphonic acid, 29.3 g of acrylic acid and 108 g of water and neutralized with 70 g of 20% strength sodium hydroxide solution. The mixture is heated to 80° C. under a slight stream of nitrogen, and 0.8 g of ammonium peroxodisulfate, dissolved in 16 g of water, is added dropwise over a period of 15 minutes. After the exothermic reaction has ceased, the mixture is stirred at 80° C. for another 4 hours. The colorless 20% strength polymer solution has an inherent viscosity value K between 35 and 40.

EXAMPLE 8

Copolymer prepared from isolated N-allylaminobis(methylenephosphonic acid) and acrylic acid Weight ratios and procedure as in Example 4.

EXAMPLES 9–10

Copolymers prepared from disodium N-allylamino(phenyl)methylenephosphonate and sodium acrylate As in Example 2, but using 0.72 g (Example 9) or 1.08 g (Example 10) of N-allylamino(phenyl)methylenephosphonic acid.

EXAMPLES 11 AND 12

Copolymers prepared from N-allylaminobis(methylenephosphonic acid) and methacrylic acid By the procedure described in Example 4, using 10% by weight (Example 11) or 1% by weight (Example 12) of phosphonic acid in the copolymer.

BRIEF DESCRIPTION OF THE DRAWING

The figure represents a chart depicting the calcium-binding capacity of polymer solutions prepared according to the present invention as compared to a solution of pure sodium polyacrylate in which chart the presence of free calcium ions in the compared test solutions is plotted on the ordinate and the presence of the compared polymers in parts per million is plotted on the abscissa.

WORKING EXAMPLES

1. Calcium-binding capacity and dispersion of calcium carbonate

| Tested substances: | Examples 4 and 8 (brought to a pH of 5 with NaOH solution and spray-drying of the 10% strength solution) Polyacrylic acid, sodium salt (MW 130,000) |
|---|---|

The test results using the Ca-sensitive electrode (buffer: 0.03 n NH$_4$Cl + 0.07 n NH$_3$) are shown in the figure. The two copolymers from Examples 4 and 8 bind calcium ions slightly better than pure sodium polyacrylate.

The dispersion of calcium carbonate was determined by the filtration method under the following test conditions: 4 mmol of calcium ions, 44 mmol of sodium carbonate, 2 mmol of sodium hydroxide, 250 ppm of polymer, T = 40° C.

| Product | Amount of dispersed $CaCO_3$ [%] |
|---|---|
| Example 4 (MW 170,000) | 69 |
| Example 8 (MW 170,000) | 59 |
| Polyacrylic acid, sodium salt (MW = 130,000) | 55 |

With respect to the dispersing capacity, copolymers 4 and 8 also give a better result than the polyacrylic acid, sodium salt, measured for comparison.

Using crude copolymerized phosphonic acid obtained by Example 3 does not diminish the quality compared with the use of isolated pure phosphonic acid (Example 8).

2. Builder effect

| Tested substances | Examples 4, 8, 11 and 12 (brought to a pH of 5 with NaOH solution and spray-drying of the 10% strength solution) ® Sokalan CP 5 (BASF) |
|---|---|

The washing tests were carried out in a Launderometer at 40° C. and washing time of 30 minutes. 0.5 g/l alkylbenzenesulfonate (Marlon A 350, Hüls) was used as surfactat, and the water hardness was 23° of German Hardness. The pH of the washing liquor was brought to 10 with dioute sodium hydroxide solution. 4 strips each of a standard solid cloth (WFK (Wäschereiforschung Krefeld) cotton, 10C) were used as soiled test fabric. The above-mentioned copolymers according to the invention were used as the builder and ®Sokalan CP5 (acrylic acid/maleic anhydride copolymer (70/30), BASF) as a comparison substance. The builder concentrations were 0; 0.25; 0.5; 0.75; 1; 1.5 and 2 g/l. The difference to 2 g/l was in each case made up with sodium sulfate.

The builder effect was determined by the increase in diffuse reflection of the tested fabrics. The results were interpreted in the known manner.

| Builder | Diffuse reflection values Builder concentrations [g/l] | | | | | | |
|---|---|---|---|---|---|---|---|
| | 0 | 0.25 | 0.5 | 0.75 | 1.0 | 1.5 | 2.0 |
| Ex. 4 | 42.7 | 42.9 | 43.5 | 44.8 | 44.9 | 49.1 | 50.5 |
| Ex. 8 | 42.4 | 42.6 | 42.7 | 43.8 | 44.3 | 47.7 | 50.2 |
| Ex. 11 | 42.5 | 42.9 | 43.8 | 43.9 | 44.4 | 45.4 | 48.2 |
| Ex. 12 | 42.5 | 42.8 | 43.0 | 43.9 | 44.5 | 45.0 | 48.4 |
| CP5 | 42.7 | 42.7 | 42.8 | 42.9 | 44.4 | 47.5 | 49.3 |

The products from Examples 4 and 8 are more effective as a builder than comparison substance ®Sokalan CP5 (BASF).

3. Co-builder effect

| Tested substances: | Examples 4, 8 (brought to a pH of 5 with NaOH solution and spray-drying of the 10% strength solution) |
|---|---|

The washing tests were carried out in a Launderometer at 40° C. and a washing time of 30 minutes. 0.5 g/l alkylbenzenesulfonate (Marlon A 350, Hüls) and 1.5 g/l zeolite A were used as the builder system. The water hardness was 23° of German Hardness. The pH of the washing liquor was brought to 10 with dilute sodium hydroxide solution. 4 strips each of a standard soiled cloth (WFK (Wäschereiforschung Krefeld) cotton, 10C) were used as soiled test fabric. The above mentioned copolymers according to the invention were used as the co-builder.

The builder concentrations were 0; 0.25; 0.5; 0.75; 1; 1.5 and 2 g/l. The difference to 2 g/l was in each case made up with sodium sulfate.

The co-builder effect was determined by the increase in diffuse reflection of the tested fabrics. The results were interpreted in the known manner.

| Builder | Diffuse reflection values Builder concentrations [g/l] | | | | | | |
|---|---|---|---|---|---|---|---|
| | 0 | 0.25 | 0.5 | 0.75 | 1.0 | 1.5 | 2.0 |
| Ex. 4 | 44.4 | 45.1 | 46.2 | 47.4 | 48.3 | 49.5 | 49.9 |
| Ex. 8 | 44.4 | 45.1 | 46.3 | 48.3 | 49.1 | 50.6 | 52.2 |

Comparable results were obtained by using a layered silicate of the SKS6 type (Hoechst) instead of the zeolite.

4. Peroxide-stabilizing effect (accelerated test)

| Tested substances: | Example 4 (brought to a pH of 5 with NaOH solution and spray-drying of the 10% strength solution) |
|---|---|

The peroxide-stabilizing effect of the copolymers according to the invention was investigated in aqueous alkaline hydrogen peroxide solutions containing metal ions by measuring the drop in hydrogen peroxide concentration as a function of time in the presence of a complexing agent.

For this purpose, 1 l of distilled water was initially introduced into a beaker, and 20 ml of a 0.1% strength copper sulfate solution and 6 g of sodium hydroxide were added. After adding the complexing agent, the solution was temperature-controlled at 70° C., 30 g of a 30% hydrogen peroxide solution were then added, and the measuring period was started. The hydrogen peroxide content of the solution was determined at 2 minute intervals by iodometric titration with sodium thiosulfate solution. After 10 minutes, the following residual amounts of hydrogen peroxide were found:

| Complexing agent | Residual amount of $H_2O_2$ |
|---|---|
| none | 0% |
| 1 g of copolymer Ex. 8 | 45% |

The copolymer according to the invention is a peroxide stabilizer.

5. Effect as scale inhibitor

| Tested substances: | Examples 2, 9, 10 ® Dodiscale 2849 (polyacrylic acid, ammonium salt) ® Dodiscale 2870 (phosphonic acid, ammonium salt) |
|---|---|

The test procedure used was the NACE Standard Test TM 0374-79. This simple static testing method was developed specifically for the use of scale inhibitors in crude oil fields as a screening method.

Procedure:

The following solutions were used: CaCO₃ precipitation test

Ca²⁺ sol.: 12.15 g/l CaCl₂ 2 H₂O; 3.68 g/l MgCl₂ 6 H₂O; 33 g NaCl

HCO₃⁻ sol.: 7.36 g/l NaHCO₃; 0.0294 g/l Na₂SO₄; 33 g of NaCl CO₂-saturated.

CaSO₄ precipitation test

Ca²⁺ sol.: 7.5 g/l NaCl; 11.1 g CaCl₂ 2 H₂O

SO₄²⁻ sol.: 7.5 g/l NaCl; 10.66 g/l Na₂SO₄

Sample preparation for CaCO₃ test

Mix 1% strength inhibitor solution with 50 ml of HCO₃⁻ sol., then add 50 ml of Ca²⁺ sol. and mix again.

Sample preparation for CaSO₄ test

Mix 1% strength inhibitor solution with 50 ml of SO₄²⁻ sol., then add 50 ml of Ca²⁺ sol. and mix again.

The CaCO₃- and CaSO₄-supersaturated solutions were left in a drying cabinet at 70° C. in sealed 100 ml bottles (DIN 250 DAB) for 24 hours. The Ca⁺⁺ remaining in solution was then determined by complexometry with 0.01 mol/l IDRANAL III (Riedel de Haen, Germany, which is the sodium salt of ethylene diamine-tetra-acetic acid and indicator/buffer tablets.

Concentrations of tested substance: 1 3 10 30 ppm
Formula for determining the dispersing effect I (%)

$$I = \frac{C_v - C_F}{C_t - C_F} \cdot 100$$

$C_v$ = Ca²⁺ concentration in the presence of the inhibitor $C_F$ = Ca²⁺ concentration in the absence of the inhibitor $C_t$ = Ca²⁺ overall concentration Using the customary procedure, 1 ml of buffer solution was removed and the following consumption was determined with 0.01 mol/l Idranal III:

|  | CaCO₃ | CaSO₄ |
|---|---|---|
| $C_t$ (theoretical) | 5.04 ml | 3.80 ml |
| $C_F$ (experimental) | 3.3–3.5 ml | 2.6–2.8 ml |
| $C_v$ (variable) | 3.3–5.0 ml | 3.0–3.8 ml |

®Dodiscale 2849 and ®Dodiscale 2870 (Hoechst) were tested as comparison products.

Dispersing effect I [%] for calcium carbonate

| Scale inhibitor | Concentrations of the inhibitor [ppm] | | | |
|---|---|---|---|---|
|  | 1 | 3 | 10 | 30 |
| Ex. 2 | 26 | 41 | 61 | 90 |
| Ex. 9 | 17 | 30 | 63 | 91 |
| Ex. 10 | 24 | 35 | 46 | 91 |
| ® Dodiscale 2849 | 43 | 62 | 67 | 80 |
| ® Dodiscale 2870 | 44 | 63 | 72 | 88 |

Dispersing effect I [%] for calcium sulfate

| Scale inhibitor | Concentrations of the inhibitor [ppm] | | |
|---|---|---|---|
|  | 1 | 3 | 10 |
| Ex. 2 | 95 | 99 | 99 |
| Ex. 9 | 93 | 98 | 99 |

-continued

| Scale inhibitor | Concentrations of the inhibitor [ppm] | | |
|---|---|---|---|
|  | 1 | 3 | 10 |
| Ex. 10 | 90 | 98 | 98 |
| ® Dodiscale 2849 | 88 | 98 | 99 |
| ® Dodiscale 2870 | 80 | 95 | 98 |

Copolymers 2, 9 and 10 are in some cases more effective scale inhibitors than the sodium salts of the pure polyacrylic acids or the sodium salts of the pure phosphonic acids.

What is claimed is:

1. A copolymer comprising 0.1%–99.9% by weight of one or more monomers of the following structural formula I

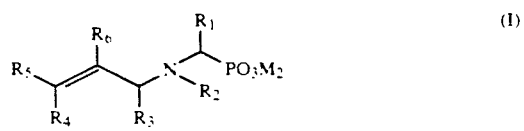

in which

R₁ is hydrogen, C₄-C₁₀-alkyl, phenyl, naphthyl, methylphenyl, hydroxyphenyl, methoxyphenyl, methylnaphthyl, hydroxynaphthyl or methoxynaphthyl, R₂ is hydrogen or a group of the formula —CH₂PO₃M₂, R₃, R₄, R₆ are hydrogen or methyl, R₅ hydrogen, C₁-C₄-alkyl or phenyl, and M is hydrogen or sodium, potassium or ammonium cation, and 99.9%–0.1% by weight, of one or more monomers of the formula $$R'_1R'_2C=CR'_3X \qquad (II)$$

in which

R₁ is hydrogen or a group of the formula —COOM,

R₂ is hydrogen, phenyl or a group of the formula —COOM,

R₃ is hydrogen, methyl or a group of the formula —COOM or —CH₂COOM,

X is a group of the formula —COOM or

R₂ and R₃, together are a C₄-alkyl radical or

R₁ and X together are a group of the formula

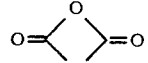

or

R₃ and X together are a group of the formula

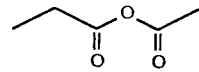

2. A process for the preparation of a copolymer as claimed in claim 1, which comprises polymerizing compounds of the formula I with compounds of the formula II.

3. The process as claimed in claim 2, wherein the polymerization is carried out in the presence of sodium sulfate.

4. A copolymer as claimed in claim 1 wherein the amount of said one or more monomers of Formula I is 1-50% by weight.

5. A copolymer as claimed in claim 1 wherein the amount of said one or more monomers of Formula II is 99-50% by weight.

6. A process for the preparation of a copolymer as claimed in claim 4, which comprises polymerizing compounds of the formula I with compounds of the formula II.

7. A process for the preparation of a copolymer as claimed in claim 5, which comprises polymerizing compounds of the formula I with compounds of the formula II.

* * * * *